United States Patent [19]
McGowan et al.

[11] Patent Number: 5,323,636
[45] Date of Patent: Jun. 28, 1994

[54] DUAL-CHANNEL FLEXURAL ACOUSTIC WAVE CHEMICAL SENSOR

[75] Inventors: Raymond C. McGowan, Neptune; Elio A. Mariani, Hamilton Square, both of N.J.

[73] Assignee: The United States of America as represented by the Secretary of the Army, Washington, D.C.

[21] Appl. No.: 77,168

[22] Filed: Jun. 11, 1993

[51] Int. Cl.$^5$ .............................................. G01N 29/02
[52] U.S. Cl. ................................ 73/24.01; 73/24.06; 310/313 R
[58] Field of Search .................... 73/24.01, 24.06; 310/313 R, 313 B

[56] References Cited

U.S. PATENT DOCUMENTS

| | | | |
|---|---|---|---|
| 4,361,026 | 11/1982 | Muller et al. | 73/24.01 |
| 4,598,224 | 7/1986 | Ballato | 73/24.01 X |
| 4,895,017 | 1/1990 | Pyke et al. | 73/24.06 |
| 5,076,094 | 12/1991 | Fry et al. | 73/24.06 X |
| 5,221,871 | 6/1993 | Fuchs et al. | 73/24.01 X |

FOREIGN PATENT DOCUMENTS

| | | | |
|---|---|---|---|
| 282115 | 8/1990 | Fed. Rep. of Germany | 73/24.06 |
| 248057 | 11/1991 | Japan | 73/24.01 |
| 148844 | 5/1992 | Japan | 73/24.01 |
| 1681229 | 9/1991 | U.S.S.R. | 73/24.01 |

*Primary Examiner*—Hezron E. Williams
*Assistant Examiner*—Joseph W. Roskos
*Attorney, Agent, or Firm*—Michael Zelenka; William H. Anderson

[57] ABSTRACT

A dual channel flexural device is fabricated on a gallium arsenide (GaAs) substrate that includes a pair of elongated active vibrating (GaAs) bars formed in the substrate that serve as acoustic waveguides. One of the bars serves as a reference channel, while the other bar is covered with a chemically sensitive coating and operates as a sensing channel. A pair of pseudo-surface acoustic wave (SAW) transducers serving as input and output transducers are located at each end of the bars. Each of the transducers is comprised of discontinuous U-shaped elements having dimensions and mutual separations of one half the acoustic operating wavelength formed on one side of the substrate while ground electrodes are formed thereunder on the opposite side of the substrate. When the transducers are energized, a flexural motion in the bars is set up, causing the bars to vibrate. The vibration of the chemically coated bar changes in response to absorption of vaporous contaminants providing a device which operates in a differential mode for chemical vapor sensing.

14 Claims, 2 Drawing Sheets

DUAL-CHANNEL FLEXURAL ACOUSTIC WAVE CHEMICAL SENSOR

GOVERNMENT INTEREST

The invention described herein may be manufactured, used and licensed by or for the Government of the United States of America without the payment to us of any royalties thereon or therefor.

BACKGROUND OF THE INVENTION

1. Field of the Invention

This invention relates generally to chemical vapor detection apparatus and more particularly to a highly sensitive chemical sensor fabricated on a semi-insulating gallium arsenide substrate.

Chemical vapor detectors consisting of bulk or surface acoustic wave devices are generally known and are typically fabricated on quartz. Such devices, however, must be used in a hybrid circuit configuration in order to achieve a desired chemical detecting function. Examples of such detectors/sensors are described in U.S. Pat. No. 5,076,094, issued to Fry et al on Dec. 31, 1991 and entitled "Dual Output Acoustic Wave Sensor For Molecular Identification," and U.S. Pat. No. 4,895,017, issued to Pyke et al in January, 1990 and entitled, "Apparatus and Method for Early Detection and Identification of Dilute Chemical Vapors," both of which are incorporated herein by reference.

SUMMARY OF THE INVENTION

Accordingly, it becomes an object of the present invention to provide an improvement in chemical vapor detectors.

It is another object of the invention to provide a more sensitive chemical sensor which permits the realization of a completely monolithic integrated chemical vapor detector on a single acousto-electronic chip.

It is a further object to provide a chemical vapor detector which is fabricated on a gallium arsenide substrate.

These and other objects are achieved by a dual channel flexural device fabricated on a gallium arsenide (GaAs) substrate that includes a pair of elongated active vibrating (GaAs) bars formed in the substrate that serve as acoustic waveguides. One of the bars serves as a reference channel, while the other bar is covered with a chemically sensitive coating and operates as a sensing channel. A pair of pseudo-surface acoustic wave (SAW) transducers serving as input and output transducers are located at each end of the bars. Each of the transducer pair is comprised of a discontinuous set of U-shaped elements having dimensions and mutual separations of one half the acoustic operating wavelength formed on one side of the substrate while a ground electrode is formed thereunder on the opposite side of the substrate. When the transducers are energized, a flexural motion is set up in the bars, causing the bars to vibrate. The vibration in the chemically coated bar changes in response to absorption of vaporous contaminants providing a device which operates in a differential mode for chemical vapor sensing.

BRIEF DESCRIPTION OF THE DRAWING

The following detailed description of the invention will be more readily understood when considered in conjunction with the accompanying drawing wherein.

DETAILED DESCRIPTION OF THE INVENTION

Figures 1A, 1B:
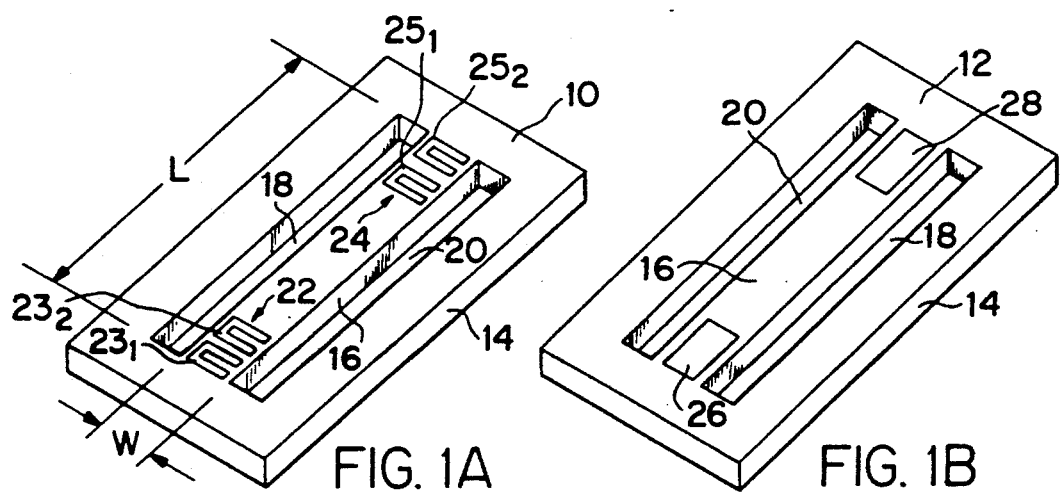
FIGS. 1A and 1B are perspective top and bottom views, respectively, of a single channel of the basic flexural wave device in accordance with the invention.

Referring now to the drawings wherein like reference numerals refer to like components throughout, reference is first made to FIGS. 1A and 1B wherein there is depicted the structural features and the top and bottom surfaces 10 and 12 of a basic flexural acoustic wave device fabricated on a gallium arsenide (GaAs) substrate 14. The structure includes an active vibrating bar section 16, designed to support the flexural wave, of generally rectangular cross section and of length L that is located between two elongated slots 18 and 20. The bar section 16 serves as an acoustic waveguide between an input and an output pseudo surface acoustic wave (SAW) acoustic transducer 22 and 24 for a flexural acoustic wave propagating along the acoustic waveguide member 16. Each of the transducers 22 and 24, moreover, includes a pair of discontinuous members comprising adjacent U-shaped metallization elements $23_1$, $23_2$ and $25_1$, $25_2$ as shown in FIG. 1A located on the top surface 10 and which form a grating type structure. On the bottom surface 12, as shown in FIG. 1B, a pair of ground electrodes 26 and 28 are formed beneath the grating members $23_1$, $23_2$ and $25_1$, $25_2$, completing the input and output transducer structure.

Figure 2:
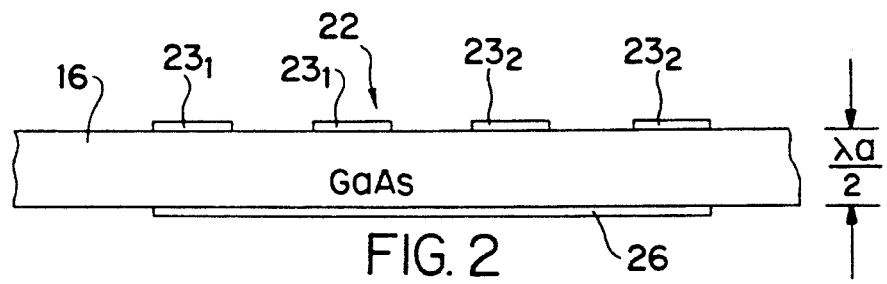
FIG. 2 is a partial central longitudinal cross section of the device shown in FIGS. 1A and 1B and being further illustrative of one of the acoustic transducers located at the ends thereof.
Figure 3:
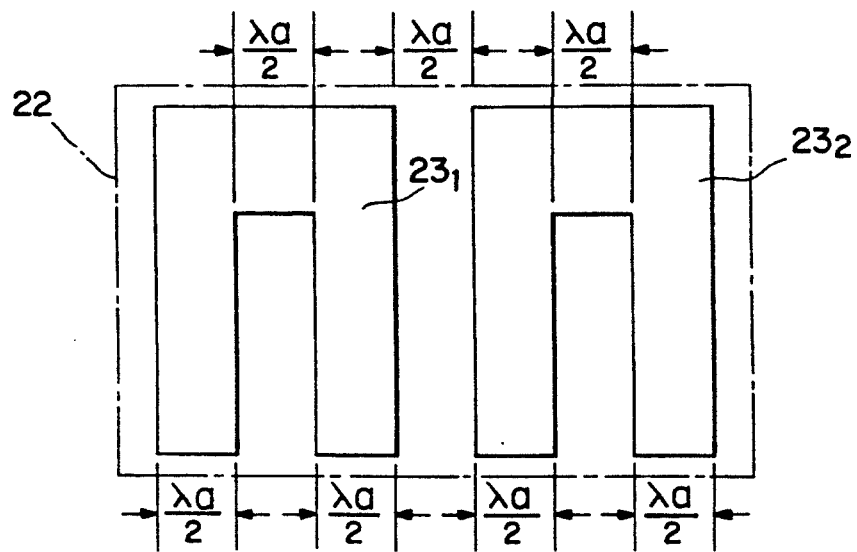
FIG. 3 is an enlarged top plan view further illustrative of the structure of the top portion of one of the transducers shown in FIG. 1A.

FIG. 2 is illustrative of a cross sectional view of one of the transducer structures 22, while FIG. 3 comprises a top planar view thereof. As shown in FIG. 2, the GaAs substrate 14 has a thickness dimension of $\lambda a/2$ where $\lambda a$ is the acoustic wavelength of an acoustic wave to be propagated along the waveguide section 16. As shown in FIG. 3, the dimensions of the U-shaped elements, for example, the members $23_1$ and $23_2$ include $\lambda a/2$ widths and spacings, with their open end portions facing the slot 20. An acoustic grating is provided thereby having a period of $\lambda a/2$. The same dimensions exist for the transducer elements $25_1$ and $25_2$ of the output transducer 24.

Figure 4:
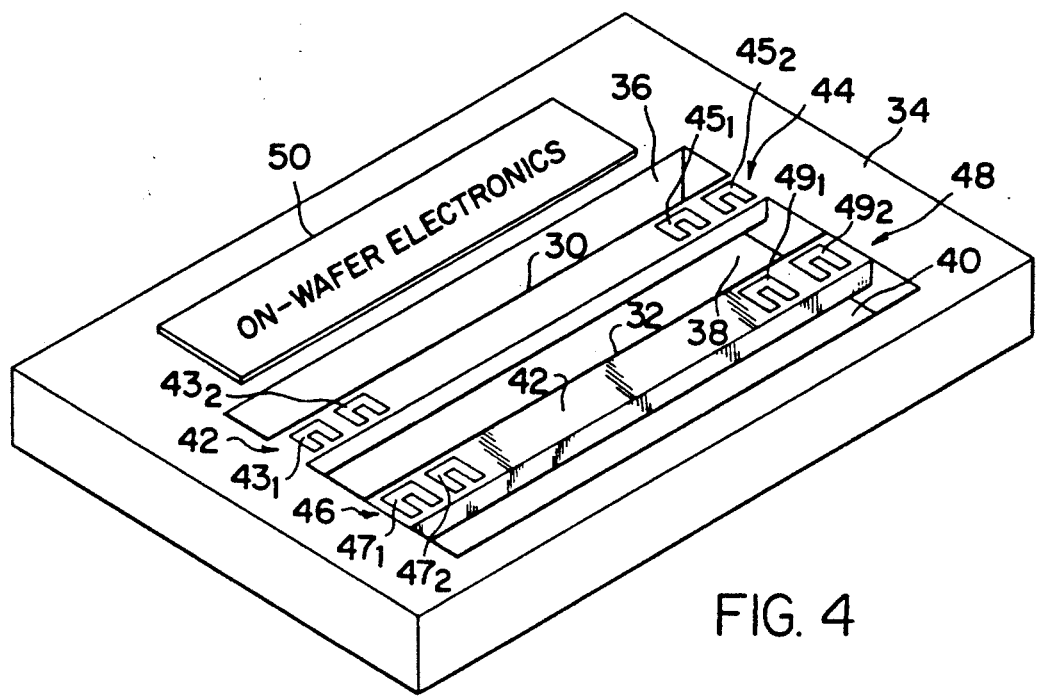
FIG. 4 is a perspective view generally illustrative of the preferred embodiment of the invention.

Turning attention now to the preferred embodiment of the subject invention, and more particularly to FIG. 4, shown thereat is a dual channel, flexural acoustic wave chemical sensor which is comprised of two vibrating bar sections 30 and 32 formed in a GaAs substrate 34 and having a reduced thickness relative to that of the substrate. Three elongated slots 36, 38 and 40 accordingly appear in the substrate 34 adjacent the bars 30 and 32. One of the bars 32 is additionally completely covered, on all four sides of the guide, with a chemically selective coating or film 42, while the other bar 30 is left uncoated and serves as a reference. Preferably, the chemical coating 42 should coat all three exposed sides of the bar 32. Those skilled in the art will be able to select the chemical coating from those materials that are used for similar purposes in the art. Examples of these materials include polymers that exhibit rapid diffusion properties such as polysiloxone, polybutadiene, and polyisoprene.

The mutual separation of the bars 30 and 32 provided by the middle slot 38 is in the order of several wavelengths($\lambda$) in order to reduce any cross talk or interaction between channels. An acoustic impedance mismatch can also be provided to reduce cross talk by altering the thickness dimensions of the bar sections 30 and 32, relative to thickness of the substrate 34.

As before, each of the GaAs bar sections 30 and 32 is provided with an acoustic transducer structure at each end as shown with respect to the basic acoustic wave device depicted in FIGS. 1A and 1B. In the preferred embodiment, the reference acoustic waveguide bar section 30 includes an input transducer 42 including a pair of U-shaped elements $43_1$ and $43_2$ and an output transducer 44 including a pair of U-shaped elements $45_1$ and $45_2$. Likewise, the coated acoustic waveguide bar 32 includes an input transducer 46 having a pair of transducer elements $47_1$ and $47_2$ and an output transducer 48 likewise including a pair of U-shaped transducer elements $49_1$ and $49_2$. All of the transducer element pairs 42, 44, 46 and 48 also include an underlying ground electrode such as that shown in FIG. 2, by reference numeral 26. It should also be noted that the substrate 34 also includes a region adjacent the slot 36 for on-wafer electronics circuitry 50, which is shown in FIG. 5.

In operation, the flexural acoustic wave device shown in FIG. 4 when used to operate as a chemical sensor, is based on the flexural motion of an acoustic wave propagating the length of the relatively thin GaAs waveguide sections 30 and 32. Each waveguide section 30 and 32, in effect, comprises a thin plate, $\lambda a/2$ thick, having free surfaces exposed on four sides, with flexural motion being generated by the respective pairs of input electrodes $43_1$, $43_2$ and $47_1$ and $47_2$ and ground planes, not shown, being driven mutually out of phase in order to set up a flexural motion in the propagation region, between the input and output transducers 43, 44 and 46, 48. Excitation of the flexural acoustic wave depends on the weak piezoelectric coupling of semi-insulating GaAs substrate. When RF input signals are applied, out of phase, to the two input transducers for both the coated and uncoated waveguide sections 30 and 32, flexural waves are generated which propagate across the length of each of the acoustic waveguide bars 30 and 32 to the respective output transducers 44 and 48. When the channel coated bar 32, for example, is exposed to a vaporous chemical contaminant to which it is sensitive, the thin film 42 formed to have a thickness which is less than 1% of the $\lambda a$, chemisorbs a quantity of the gaseous substance causing an increase in the film mass. This increase in mass of the coated waveguide bar 32 brought about by absorption of the vaporous contaminant leads to a reduction of the acoustic wave velocity in the coated waveguide bar 32 and a corresponding decrease in the detected output frequency of the bar.

This operational characteristic provides the basis for chemical sensing; however, certain inherent limitations exist due to the relatively poor frequency stability which occurs as a function of temperature. In the subject invention, however, this shortcoming is overcome in two ways. First, the configuration shown in FIG. 4 is operated in a differential mode wherein the absolute frequency from the coated channel 32 is subtracted from the absolute frequency of the reference channel 30, thus eliminating the dynamic parameters of frequency change caused by temperature, humidity, pressure, etc. Secondly, due to the fact that the embodiment of the invention shown in FIG. 4 is fabricated in GaAs, the static parameters of change, such as coating thickness, fabrication differences between the two channels can easily be compensated via the on-wafer electronics 50.

Figure 5:
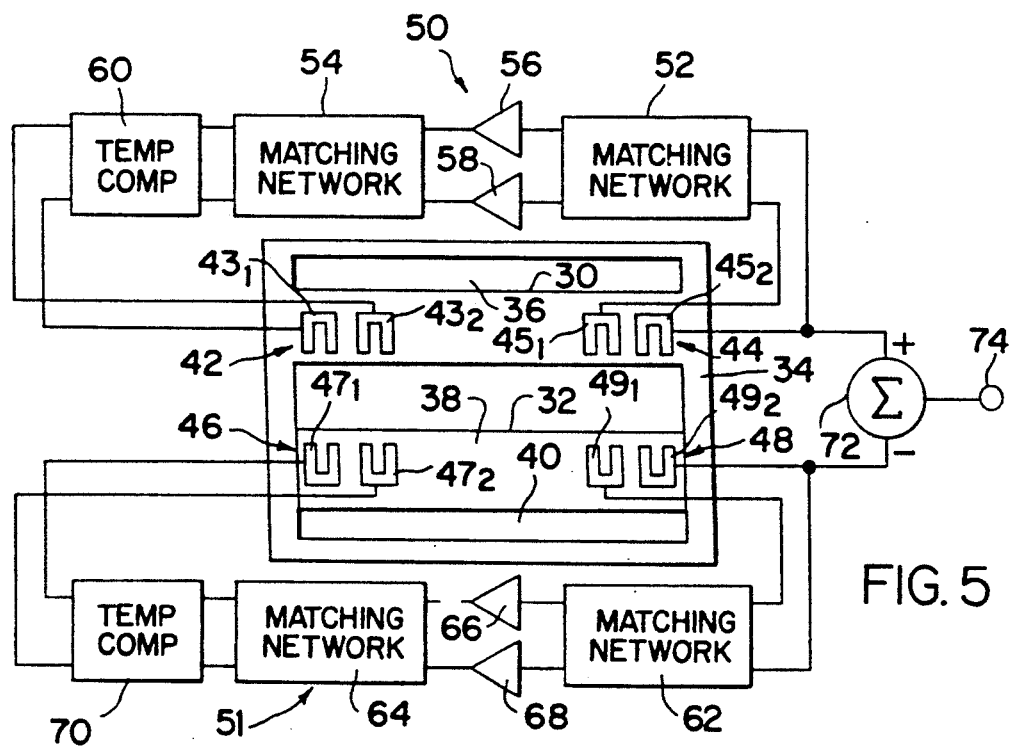
FIG. 5 is a block diagram illustrative of the electronic operation of the embodiment shown in FIG. 4.

Referring now to FIG. 5, although an energizing input source for the input transducers 42 and 46 is not shown, a feedback network 50 is provided between the output transducers 44 and 48 back to respective input transducers 42 and 46. As shown, output transducer elements $45_1$ and $45_2$ are connected to a first matching network 52 which couples to a second matching network 54 via a pair of operational amplifiers 56 and 58. The second matching network 54 is coupled to a temperature compensation device 60 which couples back to the input transducer elements $43_1$ and $43_2$. In a like manner, output transducer elements $49_1$ and $49_2$ are coupled to a third matching network 62 in a second feedback network 51 which couples to a fourth matching network 64 via a pair of operational amplifiers 66 and 68. The fourth matching network 54 is coupled to a second compensation device 70 which couples back to the input transducer elements $47_1$ and $47_2$. Further as shown in FIG. 5, a summation network 72 is being connected to the output transducer elements $45_2$ and $49_2$ so that a differential frequency output is provided at terminal 74.

The structure as shown in FIG. 4 provides several important features which provides an improvement over known prior art surface acoustic wave sensors. The configuration of FIG. 4 results in a high overtone flexural acoustic wave chemical sensor which exhibits two characteristics that makes it relatively more sensitive at a given frequency. First of all, because of the thin rectangular GaAs bar type waveguide is in flexure, all four sides of the active region contribute to the sensitivity of the device, whereas in a conventional SAW sensor, only the active region on the top surface contributes to the sensitivity of the device. Secondly, the accentuated motion of the flexure across the relatively thin GaAs bar waveguide will result in increased sensitivity. Also, the capability of placing the temperature compensation electronics on the same substrate enhances the packaging aspect of providing an integrated device on a common substrate.

Having thus shown and described what is at present considered to be the preferred embodiment of the subject invention, it should be noted that the same has been made by way of illustration and not limitation. Accordingly, all modifications, alterations and changes coming within the spirit and scope of the invention are herein meant to be included.

We claim:

1. An acoustic wave chemical sensor comprising:
   a semiconductor substrate formed from gallium arsenide;
   at least one elongated acoustic waveguide section of predetermined length, and having a plurality of free surfaces formed in the substrate, said waveguide section being freely vibratory between an input and an output end, wherein said waveguide section comprises a vibratory bar of generally rectangular cross-section and wherein said waveguide section is comprised of gallium arsenide;

acoustic wave transducer means formed on said substrate at said input end and said output end for generating and receiving an acoustic flexural wave of a predetermined frequency propagating the length of said waveguide section; and a chemical coating formed on at least one of said free surfaces and being operable to absorb a chemical substance to which the waveguide section is exposed and change said predetermined frequency due to a change in the mass of said coating, thereby providing an indication of the presence of said chemical substance.

2. The sensor as defined by claim 1 wherein said transducer means comprise pseudo-surface acoustic wave devices.

3. The sensor as defined by claim 1 wherein each said transducer means is comprised of a discontinuous grating structure on one surface of said substrate and ground plane at the location of the grating structure on a surface of said substrate opposite said one surface.

4. The sensor as defined by claim 3 wherein said substrate has a thickness dimension of $\lambda a/2$ land said grating structure comprises a plurality of generally U-shaped elements having width dimensions and mutual spacings of $\lambda a/2$, where $\lambda a$ is the acoustic wavelength of an acoustic flexural wave propagating on said waveguide section, thereby providing a grating structure having a period of $\lambda a/2$.

5. An acoustic wave chemical sensor, comprising:
a semiconductor substrate;
a pair of elongated acoustic waveguide sections having a plurality of free surfaces of predetermined equal length formed in the substrate, said waveguide sections being mutually separated and freely vibratory between respective input and output ends;

acoustic wave transducer means formed on said substrate adjacent the inner and outer ends of both said waveguide sections for generating and receiving respective acoustic flexural waves of a predetermined frequency traveling the length of said waveguide sections; and a chemical film formed on all of said free surfaces of one of said waveguide sections operating as a sensing channel so as to absorb a chemical substance to which said sensor is exposed and change said predetermined frequency propagation on said one waveguide section due to a change in the mass of said film formed thereon, said other waveguide section operating as a reference channel, and wherein both sections operate in a detected differential frequency mode to provide an indication of the presence of said chemical substance.

6. The sensor as defined by claim 5 wherein said substrate is comprised of a Group III-IV semiconductor compound.

7. The sensor as defined by claim 6 wherein said substrate is comprised of gallium arsenide.

8. The sensor as defined by claim 7 wherein both said waveguide sections comprises vibratory bars of generally rectangular section.

9. The sensor as defined by claim 8 wherein said transducer means comprises pseudo-surface acoustic wave structures.

10. The sensor as defined by claim 9 wherein said transducer means for each waveguide section comprises a discontinuous grating structure on one surface of said substrate and ground plane at the location of said grating structure on a surface of said substrate opposite said one-surface.

11. The sensor as defined by claim 10 wherein said grating structures have a period of $\lambda a/2$ and comprise a plurality of generally U-shaped elements having width dimensions and mutual spacings of $\lambda a/2$, where $\lambda a$ is the acoustic wavelength of an acoustic flexural wave propagating the respective waveguide section.

12. The sensor as defined claim 11 wherein said waveguide sections are mutually parallel and are separated by a predetermined distance so as to minimize cross talk or interaction between waveguide sections.

13. The sensor as defined by claim 12 wherein said waveguide sections are separated by at least $\lambda a$.

14. The sensor as defined by claim 11 wherein the width dimension of said waveguide sections are selectively different from the thickness dimension of said substrate for providing an acoustic impedance mismatch for reducing cross talk between said waveguide sections.

* * * * *